United States Patent

Hommeltoft

[11] Patent Number: 5,498,820
[45] Date of Patent: Mar. 12, 1996

[54] ALKYLATION PROCESS

[75] Inventor: Sven I. Hommeltoft, Hillerod, Denmark

[73] Assignee: Haldor Topsøe A/S, Denmark

[21] Appl. No.: 287,871

[22] Filed: Aug. 9, 1994

[30] Foreign Application Priority Data

Aug. 13, 1993 [DK] Denmark .................................. 0931/93

[51] Int. Cl.$^6$ .................................. C07C 2/62; C07C 2/70
[52] U.S. Cl. ........................... 585/730; 585/781; 585/462
[58] Field of Search ..................................... 585/730, 731, 585/462

[56] References Cited

U.S. PATENT DOCUMENTS

| | | |
|---|---|---|
| 3,887,635 | 6/1975 | Parker et al. |
| 4,065,516 | 12/1977 | Moser, Jr. et al. .................. 585/730 |
| 5,220,087 | 6/1993 | Berenbaum et al. ................. 585/730 |
| 5,220,095 | 6/1993 | Hommeltoft . |
| 5,414,187 | 5/1995 | King et al. ............................ 585/730 |

*Primary Examiner*—Asok Pal
*Attorney, Agent, or Firm*—Ostrolenk, Faber, Gerb & Soffen

[57] ABSTRACT

Process for the alkylation of a hydrocarbon feedstock with an olefinic alkylating agent comprising the steps of contacting the hydrocarbon feedstock and the olefinic alkylating agent with a fluorinated alkoxy alkane sulphonic acid catalyst for a sufficient time and recovering a product stream of alkylated hydrocarbons.

4 Claims, No Drawings

ALKYLATION PROCESS

The present invention relates to the alkylation of paraffinic hydrocarbons with olefinic alkylation agent in the presence of an acid catalyst.

It is well known that a number of strong acids catalyses the alkylation of isoalkanes with olefins to yield alkylate gasoline. Among the suitable catalysts is sulphuric acid, hydrogen fluoride and fluorinated sulphonic acids (U.S. Pat. No. 5,220,095).

We have now found that when the alkylation reaction is performed using a fluorinated sulphonic acid containing a weakly basic group, such as an ether linkage as catalyst, the product quality is of higher quality as compared to the product obtained by using perfluorinated sulphonic acids without a basic group under similar conditions.

Accordingly, this invention provides a process for the alkylation of a hydrocarbon feedstock with an olefinic alkylating agent comprising the steps of contacting the hydrocarbon feedstock and the olefinic alkylating agent with a fluorinated alkoxy alkane sulphonic acid catalyst for a sufficient time and recovering a product stream of alkylated hydrocarbons.

In a specific embodiment of the invention, the hydrocarbon feedstock is contacted with the catalyst in a fixed bed of solid contact material.

Suitable contact materials for use in the invention include the non-basic refractory materials, preferably silica.

It is further preferred to carry out the process as a supported liquid phase process, wherein the catalyst is moveable supported on the contact material within a confined area thereof, as described in U.S. Pat. No. 5,220,095, which by reference is incorporated herein.

With the inventive process it is possible to perform alkylation at higher temperatures or with a lower isobutane recycle than in the known processes.

The high alkylate quality as indicated by higher octane numbers is caused in part by a higher selectivity to the production of $C_8$-carbonhydrates, having higher concentrations of trimethylpentanes in the $C_8$-fraction.

EXAMPLE

A 100 ml reactor was packed with dried silica gel of the type Merck 100, 0.2–0.5 mm particle size. 6 ml perfluorinated 2-etoxyethylsulphonic acid ($C_2F_5$—O—$C_2F_4$—$SO_3H$) were introduced into the reactor. A feed stream containing 5% 2-butene in isobutane was then passed through the silica gel contact material at a feed rate of 2.5 g/min. at temperatures varying in the range 0°–30° C. The product compositions were determined by gas chromatographic analysis and the octane numbers estimated from these compositions.

The results are shown in Table 1.

TABLE 1

| Temperature, °c. | 0 | 10 | 20 | 30 |
|---|---|---|---|---|
| $C_{5-7}$ | 4 | 4 | 7 | 10 |
| $C_8$ | 91 | 90 | 85 | 79 |
| $C_{9+}$ | 5 | 6 | 8 | 12 |
| TMP's in $C_8$ | 95 | 93 | 91 | 87 |
| RON | 100 | 99 | 98 | 96 |
| MON | 97 | 96 | 95 | 94 |

I claim:

1. Process for the alkylation of a hydrocarbon feedstock with an olefinic alkylating agent comprising the steps of contacting the hydrocarbon feedstock and the olefinic alkylating agent with a fluorinated alkoxy alkane sulphonic acid catalyst for a sufficient time and recovering a product stream of alkylated hydrocarbons.

2. The process of claim 1, wherein the hydrocarbon feedstock is contacted with the catalyst in a fixed bed of solid contact material.

3. The process of claim 2, wherein the solid contact material is selected from a group of non basic refractory materials, preferably silica.

4. The process of claim 2, wherein the catalyst is moveable supported on the contact material within a confined area thereof.

* * * * *